(12) United States Patent
Ishiguro et al.

(10) Patent No.: US 6,617,603 B2
(45) Date of Patent: Sep. 9, 2003

(54) SURFACE DEFECT TESTER

(75) Inventors: Takayuki Ishiguro, Kanagawa-ken (JP); Hiroshi Nakajima, Kanagawa-ken (JP)

(73) Assignee: Hitachi Electronics Engineering Co., Ltd., Tokyo (JP)

( * ) Notice: Subject to any disclaimer, the term of this patent is extended or adjusted under 35 U.S.C. 154(b) by 0 days.

(21) Appl. No.: 10/084,911

(22) Filed: Mar. 1, 2002

(65) Prior Publication Data

US 2002/0125449 A1 Sep. 12, 2002

(30) Foreign Application Priority Data

Mar. 6, 2001 (JP) ........................................ 2001-061568

(51) Int. Cl.$^7$ .............................................. G01N 21/88
(52) U.S. Cl. .............................. 250/559.45; 356/237.2; 356/430
(58) Field of Search ................. 250/559.45, 559.46, 250/559.4, 559.21, 559.19; 356/237.2, 237.3, 430, 431, 446, 423, 243.4, 243.6, 243.8

(56) References Cited

U.S. PATENT DOCUMENTS

| | | | | |
|---|---|---|---|---|
| 4,162,126 A | * | 7/1979 | Nakagawa et al. | 356/237.2 |
| 5,875,027 A | * | 2/1999 | Ishiguro et al. | 356/243.4 |
| 5,898,491 A | * | 4/1999 | Ishiguro et al. | 356/243.4 |
| 6,057,926 A | * | 5/2000 | Horai | 356/430 |
| 6,509,966 B2 | * | 1/2003 | Ishiguro | 356/237.2 |

FOREIGN PATENT DOCUMENTS

JP  2001-174415  6/2001

* cited by examiner

Primary Examiner—Kevin Pyo
Assistant Examiner—Seung C. Sohn
(74) Attorney, Agent, or Firm—Mattingly, Stanger & Malur, P.C.

(57) ABSTRACT

An image of a scanning position on a faceplate on a light receiving region defined by an arrangement of n light receiving elements such that an amount of light received by the light receiving region becomes a peak at a center of the light receiving region in an arranging direction of the light receiving elements and is gradually reduced substantially symmetrically toward both ends thereof in the same direction. Therefore, if there is no defect in the surface of the faceplate, levels of light receiving signals of the light receiving elements arranged substantially symmetrically in position on both sides of the light receiving region with respect to the center thereof as a reference are substantially equal and there is no substantial difference therebetween. When there is a recessed or protruded defect in a scan position of the faceplate surface, the image on the light receiving region is shifted in either direction from the center by light reflected by a side slope portion of the recessed or protruded defect and the difference of the levels of the light receiving signals in symmetrical positions becomes large. The defect is detected when the difference is larger than a predetermined value.

15 Claims, 6 Drawing Sheets

DEFECT SIGNAL OF A RECESSED DEFECT

FIG. 6(b)

DEFECT SIGNAL OF A PROTRUDED DEFECT

FIG. 5(a)
23CH-APD ARRAY

SURFACE DEFECT TESTER

BACKGROUND OF THE INVENTION

1. Field of the Invention

The present invention relates to a surface defect tester and, particularly, the present invention relates to a surface defect tester for testing the flatness of a surface of a faceplate such as a magnetic disk or a glass substrate thereof, which can precisely detect the size of a recessed or protruded defect in the surface and, further, can precisely detect the size and the depth or height of such defect.

2. Description of the Prior Art

A magnetic hard disk used as a recording medium of a computer system is tested for defect and size thereof in a surface of the disk in a substrate state or a complete magnetic disk state in which a magnetic film is painted on the substrate.

The size of the recent magnetic disk is 3.3 inches or smaller and the recording density thereof is substantially increased with employment of a GMR (Giant Magneto-Resistance) head. In such magnetic disk, a glass substrate, which has thermal expansion coefficient smaller than that of the conventional aluminum substrate and is as thin as in a range from 0.6 mm to 0.8 mm, is used.

In the conventional surface defect tester, the detection of defect is usually performed by helically scanning a disk with a laser beam. However, in order to precisely detect the size of a recessed defect (such as dish type defect, pit type defectscratch type defect, or dimple defect, etc.,) or protruded defect (such as bump type defect, particle type defect, or stain type defect, etc.,), it is necessary to precisely set a illuminating angle of laser beam in a light illuminating system, a light receiving angle in a light receiving system and a voltage applied to each APD (Avalanche Photo-Diode). Further, in the conventional surface defect tester, it is necessary to optimally set parameters related to sensitivity of detection, such as gain of each of an amplifiers included in a signal processing circuit of the surface defect tester, threshold value for removing noise, and laser output of a laser light source, etc., thereof through a control panel of the surface defect tester. Incidentally, the sensitivity regulation of the surface defect tester is performed by using a practical disk having a sample defect having known size, such as dish type defect, pit type defect, scratch type defect or protruded defect having known height, as a sample disk for sensitivity calibration.

U.S. Pat. No. 5,875,027 assigned to the assignee of this application discloses such sample disk for sensitivity calibration.

On the other hand, it is required recently to improve the preciseness of defect configuration measurement and the preciseness of defect classification. However, it is impossible to precisely perform the classification of defects by the above mentioned prior art.

JP 2001-1744115A (JPA-H11-358769) assigned to the assignee of this application discloses a technique with which the above problem can be solved.

The technique disclosed in JP 2001-174415A (JPA-H11-358769) is featured by that a sensor arrangement including a plurality of APD elements is used as the light receiver and a zigzagged stripe pattern corresponding to the APD elements is provided in front of the sensor arrangement. The recessed defect and the protruded defect are detected on the basis of a difference in amount of received light between adjacent APD elements of the sensor arrangement.

However, this technique requires the zigzagged stripe pattern and a number of detection circuits are necessary to detect the difference in light amount between adjacent sensor elements.

U.S. patent application Ser. No. 9,907,713 assigned to the assignee of this application relates to a technique suitable to solve such problem. Although it is possible to detect a recessed or protruded defect without using a zigzagged stripe pattern according to this technique, a detection method thereof is different from that of the present invention.

SUMMARY OF THE INVENTION

An object of the present invention is to provide a surface defect tester capable of precisely detecting the size of recessed or protruded defect in a flat surface of a faceplate.

In order to achieve the above object, a surface defect tester according to the present invention is featured by comprising a light illuminating system for relatively scanning the surface of the faceplate by irradiating the surface with a light beam having width in a direction perpendicular to a main scanning direction, a light receiver having n light receiving elements arranged along a line perpendicular to a main scan direction, where n is an integer not smaller than 2, an optical system for focusing an image of a scanning position on the faceplate on a light receiving region defined by the n light receiving elements such that an amount of light received by the light receiving region becomes a peak at a center of the light receiving region in the arranging direction thereof and is gradually reduced substantially symmetrically toward both ends thereof in the same direction, at least two of the n light receiving elements being arranged in symmetrical positions in the light receiving region with the center of the light receiving region as a reference, and a defect detector for detecting the defect by using a difference in level between light receiving signals from the symmetrically arranged two light receiving elements as a defect detection signal, wherein the image focused on the light receiving region is moved in the arranging direction when the light receiver receives light reflected by the recessed or protruded defect by the scanning in the main scan direction.

In an embodiment, two groups each including a plurality of the light receiving elements are arranged symmetrically about the center portion of the arrangement of the light receiving elements as the reference. In this case, n is not smaller than 4. It should be noted that the principle of the present invention is to arrange at least two light receiving element one of which is arranged symmetrically to the other light receiving element. When a plurality of light receiving elements are arranged symmetrically to a plurality of other light receiving elements, total level values of light signals obtained from the plurality of light receiving elements on both sides are used.

In the present invention, the image of the scanning position on the faceplate is focused on the light receiving region defined by the n light receiving elements such that an amount of light received by the light receiving region becomes a peak at a center of the light receiving region in the arranging direction thereof and is gradually reduced substantially symmetrically toward both ends thereof in the same direction as mentioned above. Therefore, the levels of the light receiving signal from the light receiving elements arranged substantially symmetrically about the center of the light receiving region defined by the light receiving elements become substantially equal and there is no substantial difference therebetween if there is no defect in the surface of the faceplate. However, if there is a recessed or protruded defect in the scan position on the surface of the faceplate, the focused image is shifted from the center of the light receiving region in the arranging direction of the light receiving elements toward one of the ends of the light receiving region by light reflected from a slanted side face portion of the defect depending upon the type of the defect, that is, recessed type or protruded type. Therefore, the levels of the light receiving signal from the light receiving elements arranged substantially symmetrically about the center of the light receiving region become substantial and the defect is detected when the difference becomes a predetermined value or larger. Incidentally, the predetermined value is used to exclude noise, etc.

In the case where n is 2, one light receiving element is provided on one side of the light receiving region with respect to the center of the region and the other light receiving element is provided on the other side symmetrically about the center.

In the case where a plurality of light receiving elements are provided on each side of the light receiving region, a difference between a total amount of light receiving signals from the light receiving elements on one side (when the arranging direction of the light receiving elements is vertical, for example, the light receiving elements on an upper or lower side in the vertical direction and, when the arranging direction is horizontal, the light receiving elements on one side in the horizontal direction) and a total amount of light receiving signals from the light receiving elements on the other side is employed. If there is no defect in the surface of the faceplate, the difference becomes substantially zero or a value close thereto.

On the other hand, when there is a recessed or protruded defect, the focused image is shifted from the center of the light receiving region in the arranging direction of the light receiving elements toward one of the ends of the light receiving region by light reflected from a slanted side face portion of the defect depending upon the type of the defect, as mentioned above. Therefore, when the difference between the total amount of light receiving signals from the light receiving elements on one side and the total amount of light receiving signals from the light receiving elements on the other side becomes a positive or negative value larger than a predetermined value. Accordingly, it is possible to use the difference as a defect detection signal indicative of the recessed or protruded defect.

It is usual that the defect detection signal obtained from the difference between the light amounts received by the light receiving elements arranged symmetrically about the center of the light receiving region defined thereby has a positive peak and a negative peak regardless of the kind of defect, because either the recessed defect or the protruded defect has a pair of slanted side faces in the scan directions R and θ. Therefore, it is possible to detect the size of the defect on the basis of a distance between the two peaks.

The distance between two peaks is obtained by detecting scan positions (coordinates positions) at which the positive and negative peaks of the defect detection signal occur and an area of the defect can be easily calculated from a relation between the distance and the scan positions.

Further, according to the present invention, the continuity of a certain defect to another defect can be easily determined from the coordinates positions of the defects and the distances between peaks. By this determination, it is easily possible to calculate an area of a somewhat deformed defect among the recessed and protruded defects. Further, according to the present invention, it is possible to precisely detect the depth of recessed defect or the height of protruded defect by employing averages of absolute values of the positive and negative peaks.

As a result, it is possible, according to the present invention, to precisely detect the size of the recessed or protruded defect in the surface of the faceplate and to precisely detect the size and depth of the recessed defect and the size and height of the protruded defect. Therefore, it is possible to realize a surface defect tester capable of classifying the defects easily.

DETAILED DESCRIPTION OF THE PREFERRED EMBODIMENTS

Figure 1:
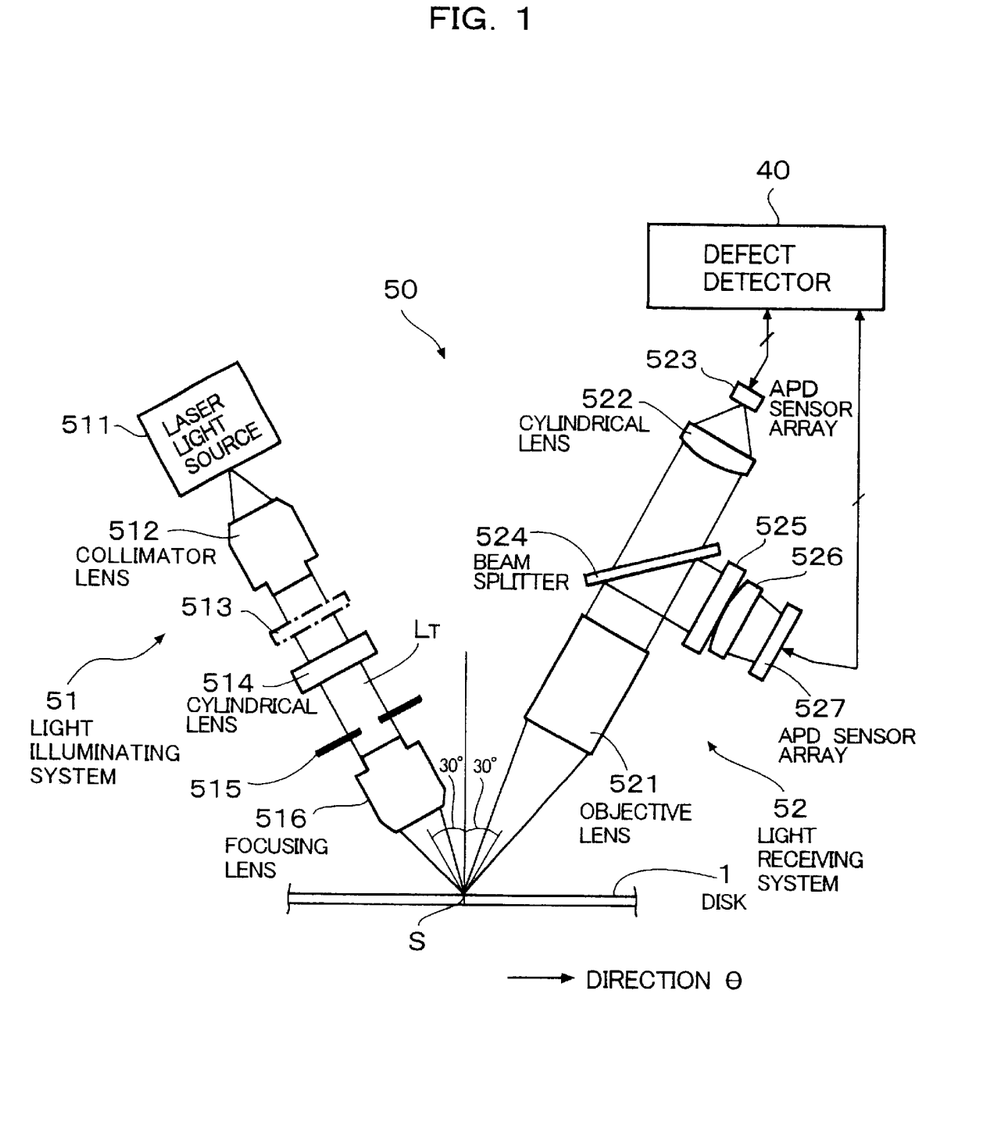
FIG. 1 illustrates a detection optical system of a surface defect tester according to an embodiment of the present invention.

FIG. 1 illustrates a surface defect tester according to an embodiment of the present invention. In FIG. 1, the surface defect tester comprises a detection optical system 50, which includes a light illuminating system 51 and a light receiving system 52. The light illuminating system 51 includes a laser light source 511, a collimator lens 512 for collimating laser beam $L_T$ from the laser light source 511 to laser light having a cross section expanded in a radial direction R perpendicular to the drawing sheet, a wavelength plate 513, a cylindrical lens 514, a pin hole 515 and a focusing lens (objective lens) 516. The collimated laser beam is focused on a surface of a disk 1 as a beam spot $S_P$ having ellipsoidal cross section (see FIG. 3(c)) through the wavelength plate 513, the cylindrical lens 514, the pin hole 515 and the focusing lens 516 with a focus point of the laser beam being shifted on the side of the beam collimator in a beam waist in the radial direction R by an offset Δd (see FIG. 3(a)).

Figure 3A:
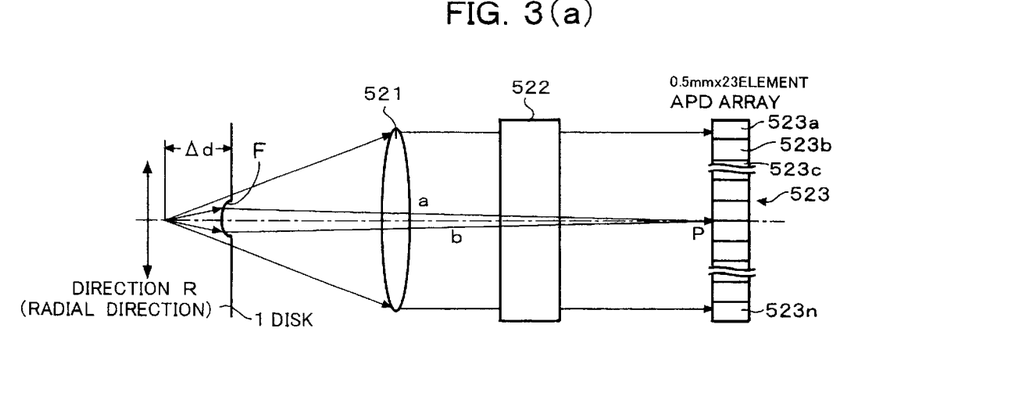
FIG. 3 illustrates light receiving systems of the detection optical system shown in FIG. 1 extended in a direction θ (circumferential direction of a disk) and in a direction R (radial direction of the disk)
Figure 3B:
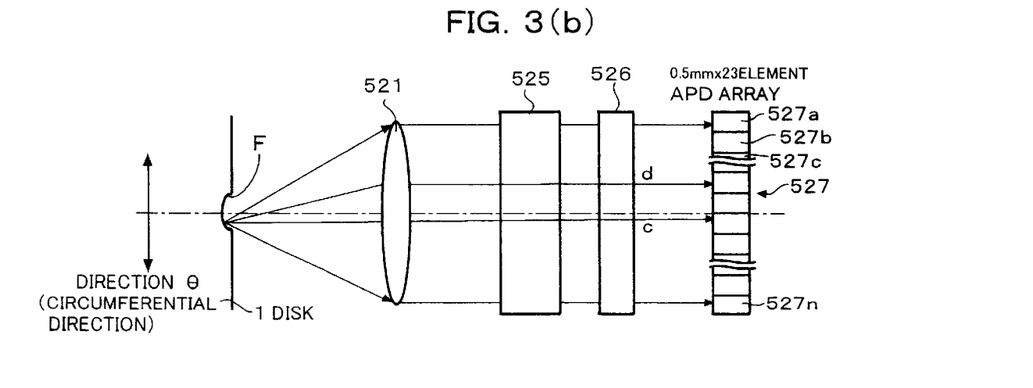
Figure 3C:
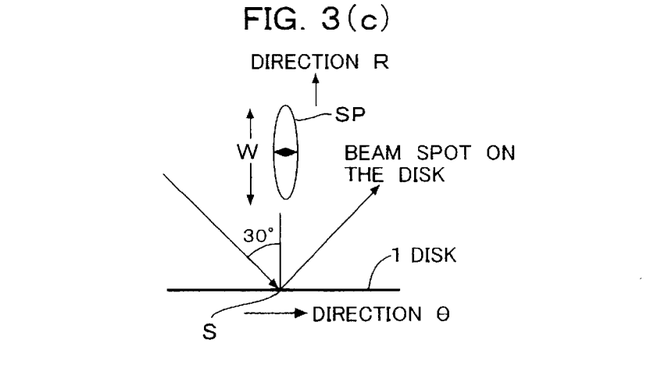

In FIG. 1, in a disk rotating direction θ parallel to the drawing sheet, laser beam $L_T$ from the cylindrical lens 514 is focused by the focusing lens 516 onto a test point S on the surface of the disk 1 (see a symbol ◆ in FIG. 3(c)). A illuminating angle thereof is about 30° with respect to a line, which is normal to the direction θ of the disk 1 as shown in FIG. 3(c). The laser beam $L_T$ has a cross sectional area having a constant width W (for example, about 100 μm to 150 μm) in the direction R, which is perpendicular to the drawing sheet. The width W substantially corresponds to a length of the arranging area of the n light receiving elements on the focusing plane in the direction R.

Incidentally, it is assumed that the disk 1 is helically scanned by the laser beam $L_T$ in the direction θ as a main scan direction and in the direction R as a sub scan direction.

The light receiving system 52 includes an objective lens 521 through which it receives a light mirror-reflected from the test point S of the disk 1. The mirror-reflected light is converted into parallel light by the light receiving system 52 and guided through a beam splitter 524 to a cylindrical lens (focusing lens) 522. The cylindrical lens 522 focuses an image of the test point S on a light receiving plane of an APD sensor array 523 corresponding to the direction R as having an ellipsoidal cross sectional area (see FIG. 4(a)).

Figures 4A, 4B:
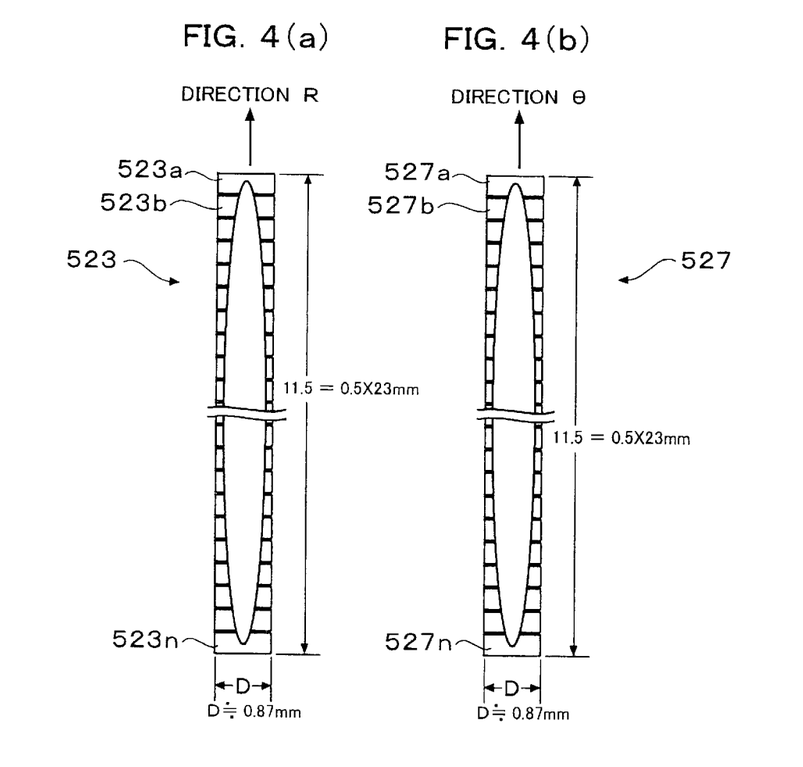
FIG. 4 illustrates a relation between an image focused on a light receiving surface in a test region and an APD sensor array.

As shown in FIG. 4(a), the APD sensor array 523 includes a plurality (n) of light receiving elements arranged along the ellipsoidal image in the direction R (major axis of the ellipsoidal area) of the disk 1 and a light receiving region is formed by the light receiving elements. Incidentally, n is an integer equal to or larger than 2 and, in this embodiment, n is 23.

The width W (about 100 μm to about 150 μm) mentioned previously corresponds to the length of about 11.5 mm of the arrangement of the light receiving elements and a beam spot $S_P$ is focused on the APD sensor array 523 in the state shown in FIG. 4(a). In this case, width of each APD sensor in the arranging direction of the light receiving elements is 0.5 mm, which corresponds to about 5 μm on the surface of the disk 1.

Further, width of the APD sensor array 523 in a direction perpendicular to the arranging direction of the light receiving elements is 0.87 mm, which corresponds to about 9 μm on the surface of the disk 1.

In addition to the light receiving system for receiving the reflected light in the direction R, a light receiving system for reflected light corresponding to the direction θ is provided separately therefrom.

That is, the light receiving system for the direction θ includes the beam splitter 524, which is provided at an angle of 45° with respect to an optical axis between the objective lens 521 and the focusing lens 522, a focusing lens 525, a planoconvex lens 526 and an APD sensor array 527. The beam splitter 524 reflects a portion of the mirror-reflected light from the test point S in a direction at 90° with respect to the optical axis. This reflected light passes through the cylindrical lens (focusing lens) 525 and the planoconvex lens 526 and becomes an ellipsoidal image having major axis extending in the direction θ. The ellipsoidal image is focused on the light receiving plane of the APD sensor array 527 arranged in the focus point of the cylindrical lens 525 as an image of the test point S. As shown in FIG. 4(b), the APD sensor array 527 includes 23 light receiving elements arranged along the direction θ (major axis direction of the ellipsoid) of the disk 1 similarly to the direction R and the light receiving area is formed by these light receiving elements.

Configuration of each of the light receiving elements of the APD sensor array 527 is similar to that of the light receiving element of the APD sensor array 523 in the direction R. However, the ellipsoidal area focused on the APD sensor array 527 formed by these light receiving elements is rotated by 90° from that shown in FIG. 4(a). That is, the light receiving area in the direction corresponding to the with of 0.87 mm of the light receiving element in the direction θ in FIG. 4(a) is expanded to the light receiving area in the direction corresponding to the width of 11.5 mm in FIG. 4(b). On the contrary, the light receiving area in the direction corresponding to the with of 11.5 mm of the light receiving element in the direction θ in FIG. 4(b) is shrunk to the light receiving area in the direction corresponding to the width of 0.87 mm in FIG. 4(a). As a result, the whole focused image of the test point S becomes ellipsoidal similar to that shown in FIG. 4(a).

Light receiving signals from the light receiving elements of the APD sensor arrays 523 and 527 are inputted to a defect detector 40.

FIGS. 3(a) and 3(b) show light receiving systems in the direction θ (parallel to the drawing sheet) and in the direction R (perpendicular to the drawing sheet), respectively.

In the light illuminating system 52, the laser beam $L_T$ from the laser light source 511 is illuminated on the test point S as an ellipsoidal beam spot $S_P$ having the width W in the direction R with the focus point being shifted on the side of the focusing lens 516 by an offset Δd from the surface of the disk 1 (see the test point S and the beam spot $S_P$ in FIG. 3(c). The mirror-reflected light from the test point S passes through the objective lens 521, the beam splitter 524 (not shown in FIG. 3(a)) and the cylindrical lens 522 and is received by the light receiving elements 523a, 523b, 523c, ... 523n of the APD sensor array 523, as shown in FIG. 3(a). Therefore, the image of the test point S is focused along the arranging direction of the light receiving elements (see FIG. 4(a)).

On the other hand, in the direction θ, laser beam $L_T$ from the laser light source 511 is focused to the test point S on the surface of the disk 1 as a spot without substantial offset (see a symbol ♦ in FIG. 3(c). The mirror-reflected light from the test point S passes through the objective lens 521, the beam splitter 524 (not shown in FIG. 3(b)), the cylindrical lens 525 and the planoconvex lens 526 to the APD sensor array 527. Therefore, the ellipsoidal image having major axis extending in the direction θ is produced and this image is focused as the image of the test point S along the arranging direction of the 517a, 527b, 527c, ... 527n of the APD sensor array 527 (see FIG. 4(b)).

Incidentally, "F" in FIGS. 3(a) and 3(b) depicts a recessed defect.

In the direction R shown in FIG. 3(a), the amount of light received by the light receiving elements is gradually reduced with increase of distance from the center of the ellipsoidal image and the distribution thereof becomes Gaussian distribution substantially and the reflected lights a and b from a bottom of the recessed defect F are received by the center portion of the APD sensor array 523 and the amount of light received thereby becomes a peak value. The peak point of the received light in the approximately Gaussian distribution is moved up or down from the point P in the drawing sheet when the APD sensor array 523 receives light reflected by side slopes of the defect F while being scanned.

Similarly to this, when the defect F is scanned in the direction θ as shown in FIG. 3(b), the peak point of the amount of received light is moved, for example, up from c to d. Since the distribution of the amount of light becomes peak at the center of the ellipsoidal image in the direction θ and gradually reduces with increase of distance from the center symmetrically, the peak point of the distribution is moved up or down on the drawing sheet when the APD sensor array 527 receives light reflected from the side slope portion of the defect F during the scanning thereof.

Figure 5A:
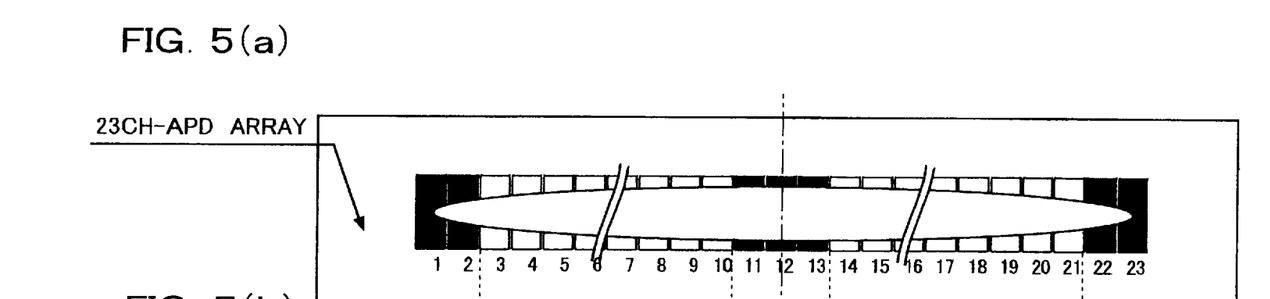
FIG. 5 illustrates a reflection light receiving state of a plurality (n) light receiving elements constituting the APD sensor array and light receiving signals corresponding thereto.

As mentioned, the image of the test point S is ellipsoidal in either direction R or θ and FIG. 5(a) shows the APD sensor array 523 or 527 shown in FIG. 3(a) or FIG. 3(b).

As shown in FIG. 5(a), the 1st, 2nd, 11th to 13th, 22nd and 23rd light receiving elements of the APD sensor array including 23 light receiving elements are masked to exclude light receiving signals from these masked light receiving elements. Alternatively, these seven light receiving elements may be removed from the APD sensor array. In this embodiment, the 3rd to 10th light receiving elements are used as a left side effective element area and the 14th to 21st light receiving elements are utilized as a right side effective element area. A sum of levels of the light receiving signals from the 3rd to 10th light receiving elements is referred to as a left sum L and a sum of levels of the light receiving signals from the 14th to 21st light receiving elements is referred to as a right sum R.

Such masking is practically performed by dumping light receiving signals from the corresponding light receiving elements. This masking may be performed for the corresponding light receiving elements in either the direction R or the direction θ. In an example to be described later, the masking in the direction R is not performed in order to improve the resolution of defect detection in the direction R.

A difference S between the left sum L and the right sum R corresponds to a difference between the sum of amounts of lights received by the light receiving elements 3 to 10 on the left side and the sum of light received by the light receiving elements 14 to 21, which are arranged substantially symmetrically to the light receiving elements 3 to 10 about the center of the APD sensor array. That is, the difference S (=L−R) becomes a defect detection signal.

Figure 5B:
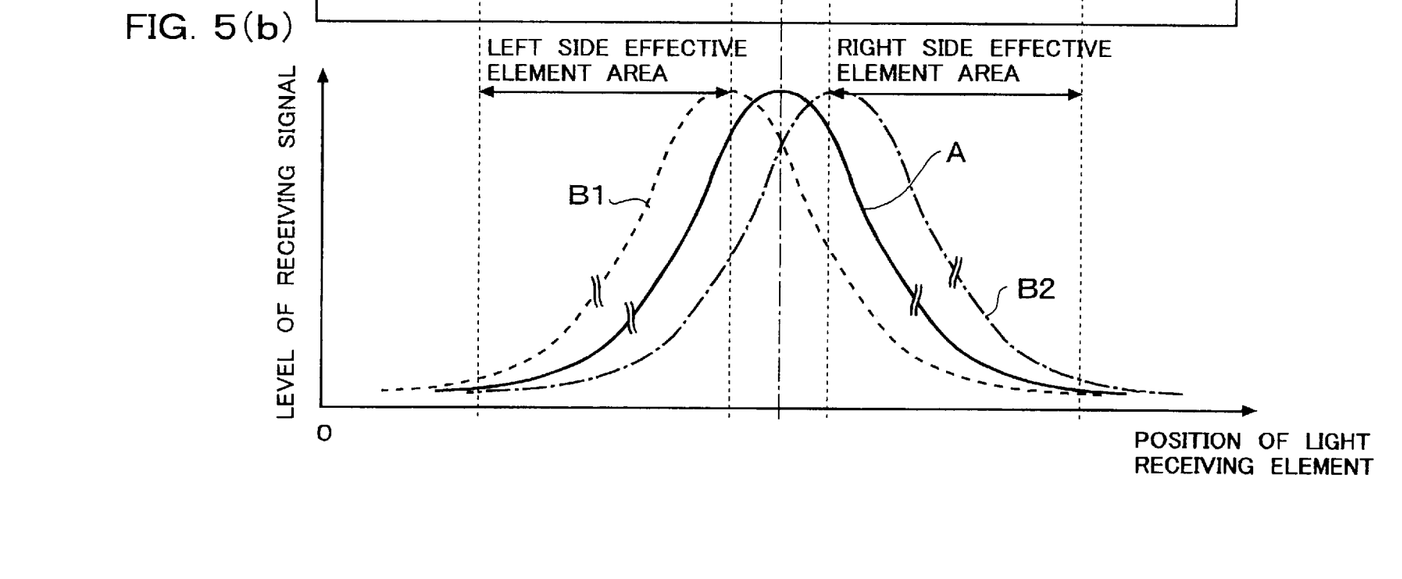

The amount of lights received by the light receiving elements in the direction R or the direction θ on a flat surface having no defect and on a bottom surface of a defect F becomes symmetrical like Gaussian distribution as shown by a solid light receiving characteristics curves shown in FIG. 5(b). That is, in FIG. 5(b), shapes of the both sides of the characteristics curve A are substantially the same. Therefore, a difference S (=L−R) between a total amount of light on one of the slopes of the characteristics curve and a total amount of light on the other slope when there is no defect becomes substantially zero or a very small.

On the other hand, if the peak point of the received light is shifted leftward, the differences becomes a positive value, which is large correspondingly to an amount of the peak shift. This is because the difference S between the total value L of the lights received by the 3rd to 10th light receiving elements and the total value R of lights received by the 14th to 21st light receiving elements becomes as shown by a dotted light receiving characteristics curve B1 in FIG. 5(b). On the contrary, if the peak point of the received light is shifted rightward, the difference becomes a negative value, which is large correspondingly to an amount of the peak shift. This is because the difference S between the total value L of the lights received by the 3rd to 10th light receiving elements and the total value R of lights received by the 14th to 21st light receiving elements becomes as shown by a chain-line light receiving characteristics curve B2 in FIG. 5(b).

That is, it is possible to detect the amount of shift of the peak portion by obtaining the difference between the slope portions of the respective light receiving characteristics curves. As will be clear from the light receiving states shown in FIGS. 3(a) and 3(b), the shift occurs when the sloped portion of the recessed or protruded defect F is scanned by laser beam $L_T$. The amount of shift in either the direction R or θ corresponds to the depth or height of the defect F.

This will be described in detail with reference to FIGS. 3(a) and 3(b). In these figures, the 1st light receiving element in FIG. 5(a) corresponds to the light receiving element 513a in FIG. 3(a) and the 23rd light receiving element in FIG. 5(b) corresponds to the light receiving element 523n. This is the same for FIG. 3(b).

The peak current at the center portion of the APD sensor array is usually obtained by the light receiving elements arranged in the center portion. When the rising side slope portion of the recessed defect F is scanned by laser beam $L_T$, the peak of the light receiving signal at the center portion is shifted rightward (downward in FIG. 3(a)). And then, the bottom of the recessed defect is scanned and the peak is returned to the light receiving element in the center portion. When the falling side slope portion of the defect is scanned by laser beam $L_T$, the peak of the light receiving signal at the center portion is shifted leftward (upward in FIG. 3(a)). And then, the laser beam goes out of the recessed defect and the peak is returned to the light receiving element in the center portion.

Figures 6A, 6B:
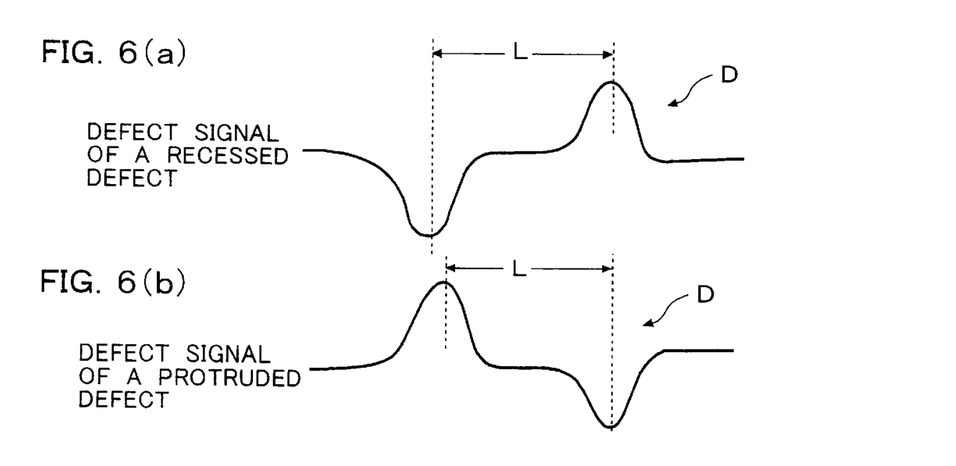
FIG. 6 illustrates a regularly reflected light by a recessed defect and a detected waveform thereof and a regularly reflected light of a protruded defect and a detected waveform thereof.

When the defect detection signal D obtained by a recessed defect is represented by an analog signal, the analog signal includes a negative peak and a positive peak following the negative peak as shown in FIG. 6(a).

In the case where the defect F is a protruded defect, when the rising side slope portion of the protruded defect F is scanned by laser beam $L_T$, the peak of the light receiving signal at the center portion is shifted leftward (upward in FIG. 3(b) in either direction R or θ). And then, it is returned to the light receiving element in the center portion. When the falling side slope portion of the defect is scanned by laser beam $L_T$, the peak of the light receiving signal at the center portion is shifted rightward (downward in FIG. 3(b)). And then, the laser beam goes out of the protruded defect and the peak is returned to the light receiving element in the center portion. The defect detection signal D in this case includes a positive peak and a negative peak following the positive peak as shown in FIG. 6(b) in either the direction R or θ.

Therefore, in FIGS. 6(a) and 6(b), a peak-to-peak distance L of the defect detection signal D in either direction R or θ corresponds to the size (width) of the defect. Further, in FIG. 6(a), the peak-to-peak distance L of the defect detection signal D corresponds to the depth of the recessed defect and, in FIG. 6(b), the peak-to-peak distance L of the defect detection signal D in either direction R or θ corresponds to the height of the protruded defect.

Since the rising side slope portion and the falling side slope portion of the recessed or protruded defect may be substantially symmetrical about a normal line of the disk, the amplitude of the defect detection signal is firstly shifted in one direction and then returned and, secondly, shifted in the other direction and then returned, so that there are a positive and negative peaks as the defect detection signal. The shifting direction for the recessed defect is opposite to the shifting direction for the protruded defect.

That is, in this case, when the first peak of the defect detection signal is negative, the defect is a recessed defect and, when the first peak of the defect detection signal is positive, the defect is a protruded defect. And, the distance L between the first peak and the second peak corresponds to the size of the defect.

The direction of the first peak and the distance between the first and second peaks are detected by a data processor 410 of the defect detector 40. The data processor 410 receives the light receiving signals from the light receiving elements 523a, 523b, 523c, . . . , 523n in the direction R and the light receiving elements 527a, 527b, 527c, . . . , 527n in the direction θ through A/D converter circuits 403a, . . . , 403n and A/D converter circuits 407a, . . . , 403n as digital values, respectively, and calculates the difference value S=L−R in each of the directions R and θ. The defect detection signals D are obtained therefrom. The positive and negative peaks of the difference value D in each direction are detected and the magnitudes of the peaks, the polarity of the first peak and the distance L between the peaks are determined in each direction. On the basis of this determination, the kind of the defect is determined and the size (height or depth) of the defect is determined on the basis of the magnitude of the difference value S. The defect detector 40 for performing these determinations will be described in detail with reference to FIG. 2.

As mentioned previously, the light illuminating system 51 provides the offset Δd of the focal point on the disk surface in the direction R. The data processor 410 can detect the kind of the defect by calculating the difference value S by utilizing a lens effect of the defect. However, the kind of the defect can be detected in the direction θ. Therefore, in the light illuminating system 51, the lens effect of the defect in the direction R is reduced by changing the value of the offset Δd, so that the image of the test region formed by the beam spot Sp and having width W in the direction R is illuminated onto the light receiving elements 523a, . . . , 523n arranged in the direction R. Therefore, the light receiving elements of the light receiving system in the direction R can detect the defect with resolutions of the elements. The defect detector 40 detects the defect under such conditions.

That is, the data processor 410 can detect very small defect in the direction R with resolution of each light receiving element and with detection sensitivity higher than that in the direction θ. In this case, however, it is impossible to determine the kind of defect in the direction R. In order to solve this problem, a detection result in the direction θ with which the kind of defect can be determined is combined. Therefore, it becomes possible to determine the kind of defect while improving the resolution of defect detection.

Figure 2:
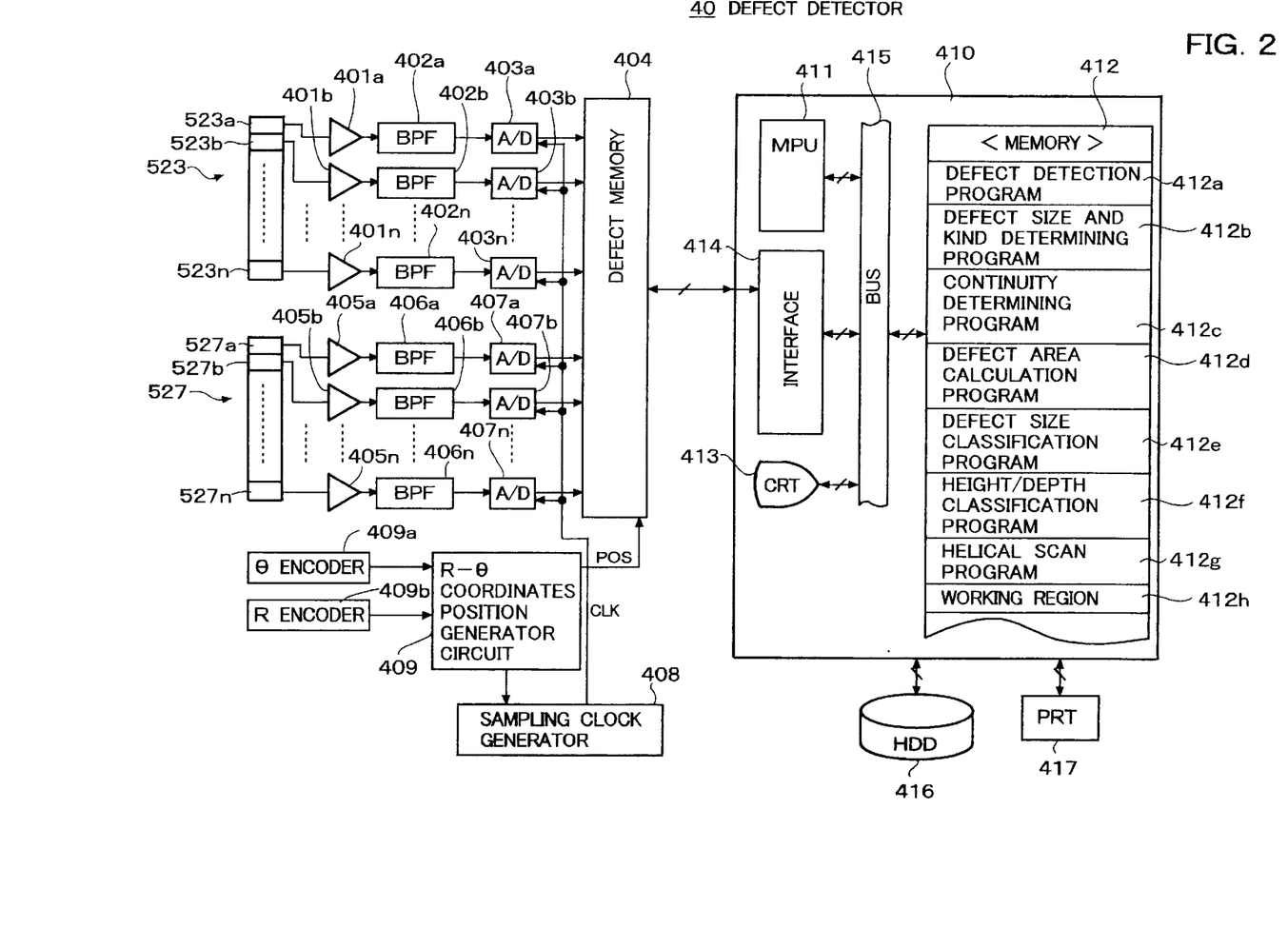
FIG. 2 is a block diagram of a defect detection processing unit of the surface defect tester shown in FIG. 1.

In FIG. 2, the 23 light receiving signals from the light receiving elements 523a, 523b, . . . , 523n of the APD sensor array 523 are transmitted through 23 channels to respective preamplifiers 401a, 401b, . . . , 401n and amplified thereby. The amplified light receiving signals are passed through band-pass filters (BPF) 402a, 402b, . . . 402n and supplied to the respective A/D converter circuits 403a, 403b, 403n for digitizing levels of the light receiving signals. The digital values of the light receiving signals are stored in corresponding address positions of a defect memory 404. A sampling clock generator circuit 408 supplies a clock signal CLK to the A/D converter circuits 403a, 403b, . . . , 403n and to the defect memory 404. That is, the A/D converter circuits 403a, 403b, . . . , 403n convert the light receiving signal levels into the digital values according to the clock signal CLK and the defect memory 404 stores the digital levels according to the clock signal CLK.

Similarly, the 23 light receiving signals from the light receiving elements 527a, 527b, . . . , 527n of the APD sensor array 527 are transmitted through 23 channels to respective preamplifiers 405a, 405b, . . . , 405n and amplified thereby. The amplified light receiving signals are passed through band-pass filters (BPF) 406a, 406b, . . . , 406n and supplied to respective A/D converter circuits 407a, 407b, . . . , 407n for digitizing levels of the light receiving signals. The digital values of the light receiving signals are stored in corresponding address positions of the defect memory 404.

The defect memory 404 stores coordinates data of a current scan position from a R-θ coordinates position generator circuit 409 together with data indicative of the digital levels of the respective light receiving signals as a two-dimensional scan coordinates position POS (defect detection position), which shows a beep spot $S_P$ in the directions R and θ.

The R-θ coordinates position generator circuit 409 generates a position signal indicative of a position at which a defect is detected on the basis of an angle pulse from a θ encoder 409a, which is indicative of an amount of rotation of the disk in the direction θ, and a pulse from a R encoder 409b, which is indicative of a moving amount in the direction R.

The defect memory 404 has two memory regions each capable of storing data corresponding to one track. At a time when data corresponding to one track is stored in one of the two memory regions of the defect memory, the one memory region is switched to the other memory region and the data stored in the one memory area is transferred to the data processor 410 through an interface 414. Data corresponding to a next track is stored in the other memory region continuously to the data stored in the one memory region. When the transfer of the data in the one memory region is completed, the data in the one memory region is erased for a storage of the data corresponding to the next track in the other memory. In this manner, data corresponding to one track and data corresponding to a next track are alternately stored in the two memory regions and transferred to the data processor 410 successively.

An operation of the data processor 410 will be described.

The data processor 410 is constructed with a MPU 411, a memory 412, a CRT display 413 and the interface 414, etc. These components are mutually connected by a bus 415.

The memory 412 stores a defect detection program 412a, a defect size and kind determining program 412b, a continuity determining program 412c, a defect area calculation program 412d, a defect size classification program 412e, a height/depth classification program 412f and a helical scan program 412g, etc., and includes a working region 412h. Various data files for classifications are stored in an external memory 416 such as HDD (Hard Disk Drive) connected thereto through the interface 414.

Incidentally, a reference numeral 417 depicts a printer (PRT) connected to the data processor 410.

The defect detection program 412a is executed by the MPU 411. That is, the MPU 411 receives data corresponding to one track through the interface 414 and stores the data in the working region 412h of the memory 412. Data in the direction R among the data corresponding to one track and stored in the working region, which have values larger than the predetermined value, are processed as defects. The thus detected defects, together with the scan coordinates position POS thereof, are stored in the external memory 416 as the defect detection data in the direction R.

As to data in the direction θ among the data corresponding to the one track stored in the working region, the total value L of levels of the light receiving signals from the 3rd to 10th light receiving elements and the total value R of levels of the light receiving signals from the 14th to 21st light receiving elements are calculated. Further, the difference value S between L and R (corresponding to the analog defect detection signals shown in FIGS. 6(a) and 6(b)) is calculated and, when the difference is equal to or larger than a predetermined difference value P, the data is determined as defect data and the polarity and the peak value thereof are determined. The polarity, the peak value and the scan coordinates position POS (detection coordinates position) thereof are stored in the external memory 416 as the defect detection data in the direction θ. Incidentally, the predetermined difference value P is a level value with which the defect is distinguished from noise.

Thereafter, the MPU 411 determines whether or not data corresponding to all of the tracks are stored in the external memory 416 and, after the processing of the data corresponding to all of the tracks is completed, the MPU 411 calls the defect distance calculation/kind determination program 412*b* and executes the latter.

The defect distance calculation/kind determination program 412*b* is executed by the MPU 411. That is, the MPU 411 reads the respective peak values of the defect data among the defect detection data in the direction θ stored in the external memory 416 and calculates the distance L between adjacent positive and negative peaks on the basis of the detection coordinates POS thereof. It is determined whether or not the distance L is equal to or smaller than a reference value Q and, when P is not larger than Q, the adjacent two peaks are determined as paired data of a defect signal corresponding to one defect shown in FIGS. 6(*a*) and 6(*b*). These peak values are stored as paired data. Further, the MPU 411 calculates a center coordinates C on the basis of the calculated distance L and the coordinates position POS at which the defect is detected. The distances L (corresponding to a length of a defect) calculated correspondingly to the paired data and the center coordinates values C thereof are stored in the memory 412 or the external memory 416 sequentially as a defect data by the MPU 411. The MPU 411 performs a similar processing for adjacent peaks of all of the defect detection data in the direction θ.

When the predetermined difference value P is larger than the reference value Q, the MPU 411 recognizes the peaks as not paired peaks but independent peaks and merely stores them in the memory 412 or the external memory 416 as defect data each having a length of zero and a coordinates value as a center coordinates of the defect.

Thereafter, the MPU 411 determines the kind of the defect, a recessed defect or a protruded defect, on the basis of the polarity of the first peak of each of the paired peaks (see FIGS. 6(*a*) and 6(*b*)). The MPU 411 stores flags indicative of the kinds of the defects in the memory 412 or the external memory 416 correspondingly to the peak values of the paired peaks.

After the pairing of defect data and the defect kind determination are completed, the MPU 411 calls the continuity determination processing program 412*c*.

The continuity determination program 412*c* is executed by the MPU 411. That is, the MPU 411 performs a determination of the continuity of defect on the basis of the distances L calculated for all of the defect data in the direction θ. This determination is performed by the MPU 411 by reading the center coordinates C and the length (distance L) of a certain defect in the direction θ, continuity of which is to be determined, and searching for defect data in positions deviated in the direction R from the main scan direction by width of substantially 115 $\mu$m ((detecting width of one light receiving element)×23=5 $\mu$m×23=115 $\mu$m) for one track in the helical scan.

And then, the MPU 411 determines whether or not the detection coordinates position of the searched defect data in the direction θ is coincident with the detection coordinates position of the certain defect within the range of the distance L in the direction θ. Upon this determination, the continuity of the defect data to the searched data adjacent thereto in the direction R with a gap of the above mentioned width in the main scan direction R therebetween is determined. Incidentally, the practical range in which the detection coordinates positions are coincident is distance L+9 $\mu$m. As mentioned previously, 9 $\mu$m is the detection width of the light receiving element in the direction θ. Defect having detection coordinates position within the range of L+9 $\mu$m is determined as defect continuous to the certain defect. The defect continuous to the certain defect is grouped with the certain defect as one defect data and is stored together with a number assigned thereto sequentially from the innermost or outermost track of the disk. In this case, since there is no continuity between a recessed defect and a protruded defect, such defects are excluded from the continuity determination processing.

And then, the MPU 411 performs the continuity determination for all of the defect data in the direction R in the similar manner. This is performed by determining whether or not there is a defect detection coordinates at a position deviated from the center of the defect in the direction R within the detection width, which is, in this embodiment, 5 $\mu$m, in the direction R and within the detection width, which is, in this embodiment, 9 $\mu$m, in the direction θ on the basis of the center coordinates C and the lengths (distances L) of the recessed and protruded defects detected in the direction θ.

In this manner, the defect continuity is determined for the defect detection data of the 23 light receiving elements in the direction R with respect to the adjacent defect data. The continuous recessed defects and the continuous protruded defects are grouped as defect data groups, respectively, and stored in the memory 412 or the external memory 416 by assigning numbers to the detected defects sequentially from the innermost or outermost track.

The MPU 411 further groups defects in the defect group in the direction θ and the defect group in the direction R, which have coordinates overlapped in a region, as another defect group. Among the defect group in the direction θ, defects, which are not grouped as one defect in the direction R are excluded from the continuous defect group in the direction θ.

With this processing, the defects are stored in the memory 412 or the external memory 416 with the numbering of the defects being changed. Since the defect detected by the light receiving elements arranged in the direction R corresponding to the area of defect is also detected in the direction θ, a double detection of the defects having same detection coordinates R-θ is excluded, resulting in an improvement of preciseness of defect detection. After this processing, the MPU 411 calls the defect area calculation program 412*d*.

The defect area calculation program 412*d* is executed by the MPU 411. That is, the MPU 411 calculates an area of grouped defects. An area of a defect whose detection signal has only one peak is calculated as a discrete defect having a width of 5 $\mu$m and a length L, that is, L×5 $\mu$m. And then, the MPU 411 calls the defect size classification program 412*e*.

The defect size classification program 412*e* is executed by the MPU 411. That is, the MPU 411 classifies the defect areas calculated as mentioned above to five classes, that is, very large, large, medial, small and very small, and stores a result of the classification correspondingly to the defect numbers thereof. And then, the MPU 411 calls the height/depth classification program 412*f*.

The height/depth classification program 412*f* is executed by the MPU 411. That is, the MPU 411 calculates an average of absolute values of a number of positive peaks and a number of negative peaks of the defect data stored in the memory 412 in the sequence of defect numbers and grouped to one. As to the defects each having two peaks and not grouped, the MPU 411 calculates an average of absolute values of the positive peaks and an average value of absolute values of the negative peaks. The MPU 411 classifies the defects to large, medial and small according to the calculated average values and stores them in the memory 412 correspondingly to the defect numbers thereof. Incidentally, the averaging of defects having only one peak is not performed. Since almost all of the detected and grouped recessed or protruded defect data have at least three peaks, it is possible to calculate a depth or height of each defect by the average value. Therefore, the detection accuracy can be improved.

Figure 7:
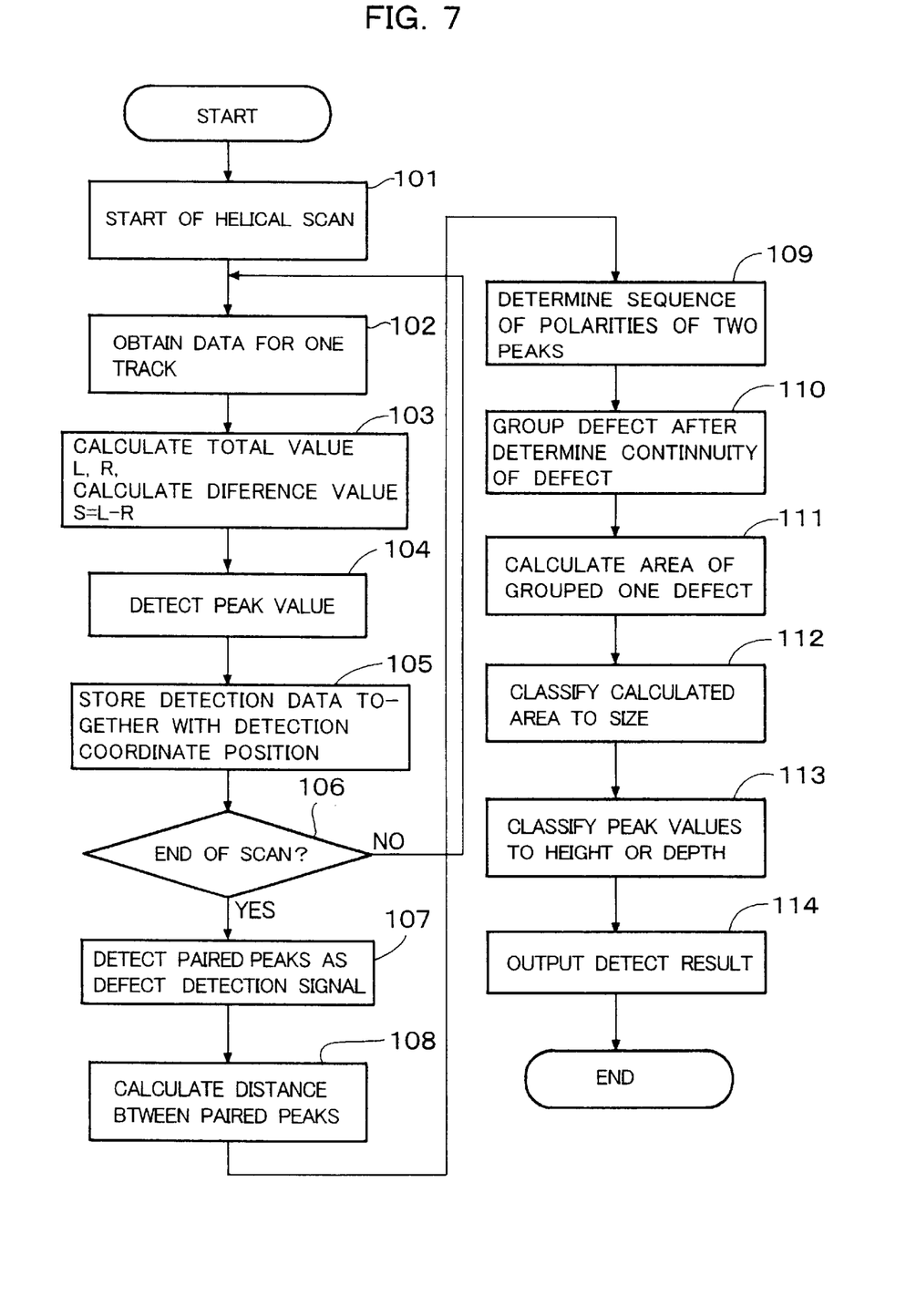
FIG. 7 is a flowchart of a defect detection processing and a defect kind determination processing of the surface defect tester shown in FIG. 1.

FIG. 7 is a flowchart of the defect detection processing in the direction θ according to the above mentioned respective programs.

First, the MPU 411 executes the helical scan program 412g to start the helical scan (step 101) and obtains data for one track (step 102). Thereafter, the MPU 411 calculates the total value L and the total value R of the light receiving signal levels from the left side light receiving elements and of the light receiving signal levels from the right side light receiving elements, which are shown in FIG. 5(a), and calculates the deference value S (=L−R) (step 103). Further, the MPU 411 detects the peak values and the polarities thereof (step 104) and stores these detection data together with detection coordinates positions corresponding to the peaks (step 105). And then, it is determined whether or not all of the tracks are scanned (step 106). When the scan of the all tracks is not completed, the operation is returned to the step 102 and, when it is completed, peaks, which are paired, are detected as the defect detection signal (step 107).

Thereafter, the distance L between the paired peaks is calculated and the center coordinates C is calculated (step 108). These data are stored at the time when these data are calculated and the kind of the defect, that is, a recessed or protruded defect, is determined on the basis of the sequence of polarities of the two peaks (step 109). And then, the continuity of the defect is determined on the basis of the distance L and the center coordinates C and the grouping of the defect is performed. Further, as mentioned previously, the continuities of all of the defect data in the direction R with respect to other defect data are determined and the grouping thereof is performed. The defect is detected in this manner (step 110).

And then, an area of the grouped one defect is calculated (step 111). The size of the defect is classified on the basis of the thus calculated area (step 112) and then the height or depth of the defect is classified on the basis of the peak values (step 113). Finally, the thus detected defects are outputted to the display 413 or the printer 417 (step 114).

Although the light receiving elements, which are masked in FIG. 5, may be removed as mentioned previously, these light receiving elements are not removed in this embodiment in order to calculate the total light receiving level by adding the light levels of all of the light receiving elements to thereby detect larger size detects. Further, it becomes possible to determinate an error detection on the basis of the total light receiving level.

The light receiving element used in the present invention may be any provided that a light receiving signal of the sloped portion of the light receiving characteristics can be obtained. Preferably, at least two pairs of light receiving elements are arranged symmetrically about the center of the light receiving element arrangement. In such case, when one light receiving element is arranged in the center and two light receiving elements are arranged in opposite ends of the light receiving region, respectively, the total number of the light receiving elements becomes at least 7.

It should be noted, however, that it is not always necessary to provide two groups each including a plurality of light receiving elements in symmetrical positions and to totalize the light receiving signal levels of the respective light receiving element groups. It may be possible to arrange two light receiving elements in symmetrical positions, respectively. In such case, at least two light receiving elements are arranged symmetrically about the center of the light receiving element arrangement.

Although, in the embodiment, the n light receiving elements are arranged in each of the directions R and θ, the number of the light receiving elements in one of the directions R and θ may be different from that in the other direction and the light receiving signals may be obtained from the light receiving elements in either the direction R or the direction θ.

Further, laser beam is used to irradiate the test surface of the disk in this embodiment. In such case, laser beam is preferably S polarized light. However, irradiating light is not limited to laser beam and white light may be used.

Further, although the present invention has been described with respect to the disk surface defect tester, the present invention can be applied to a defect test for a LCD substrate, a photo mask or a semiconductor wafer, etc. Further, although the R-θ helical scan has been described, the present invention may be applied to two dimensional X-Y scan.

What is claimed is:

1. A surface defect tester for detecting a defect in a surface of a faceplate by scanning the surface with light beam and receiving light reflected by the surface by a light receiver, comprising:

a light illuminating system for relatively scanning the surface of the faceplate by irradiating the surface with a light beam having width in a direction perpendicular to a main scanning direction;

a first light receiver composed of an arrangement of n light receiving elements, where n is an integer equal to or larger than 2;

an optical system for focusing an image of a scanning position on the faceplate on a light receiving region defined by said arrangement of said n light receiving elements such that an amount of light received by said light receiving region becomes a peak at a center of said light receiving region in an arranging direction of said light receiving elements and is gradually reduced substantially symmetrically toward both ends thereof in the same direction, at least two of said n light receiving elements being arranged in symmetrical positions in the light receiving region about said center of said light receiving region as a reference; and a defect detector for detecting the defect by using a difference in level between light signals received from said symmetrically arranged two light receiving elements as a defect detection signal, said focused image being moved in said arranging direction when said light receiver receives light reflected by a recessed or protruded defect by the scanning in said main scan direction.

2. A surface defect tester as claimed in claim 1, wherein n is an integer equal to or larger than 4 and a plurality of said light receiving elements are arranged in positions on one side of said light receiving region, wherein a plurality of said light receiving elements are arranged in symmetrical positions on the other side of said light receiving region and wherein said defect detection signal is a difference between a total value of levels of the light receiving signals from said light receiving elements on said one side and a total value of levels of the light receiving signals from said the other side.

3. A surface defect tester as claimed in claim 2, wherein said n is equal to or larger than 7 and said n light receiving elements are arranged with a predetermined interval.

4. A surface defect tester as claimed in claim 2, wherein said focused image is moved in said arranging direction by light reflected from a side slope portion of said recessed or protruded defect and said defect detector detects said recessed or protruded defect when said defect detection signal is changed in a positive or negative direction by an amount exceeding a predetermined value.

5. A surface defect tester as claimed in claim 4, wherein said faceplate is a disk, wherein the light receiving amount characteristics of said light receiving region is Gaussian distribution or the like, wherein said arranging direction of said light receiving elements is said main scan direction or a direction perpendicular to said main scan direction, wherein said defect detection signal includes a positive peak and a negative peak when said recessed or protruded defect is detected and wherein said defect detector detects one defect when a distance between said positive and negative peaks is smaller than a predetermined value.

6. A surface defect tester as claimed in claim 5, wherein said light receiving amount characteristics of said light receiving region is obtained by an ellipsoidal focused image along said arranging direction of said light receiving elements, wherein a major axis of said ellipsoidal image in coincident with a direction along a periphery of said disk or a radial direction of said disk and wherein said defect detector distinguishes between said recessed defect and said protruded defect on the basis of a sequence of said positive and negative peaks.

7. A surface defect tester as claimed in claim 5, further comprising a position signal generator circuit for generating a signal indicative of scan positions when said positive and negative peaks occur, wherein a size of a defect is determined correspondingly to a distance between the scan positions at which said positive and negative peaks occur.

8. A surface defect tester as claimed in claim 6, further comprising a position signal generator circuit for generating a signal indicative of scan positions when said positive and negative peaks occur, wherein a size of a defect is determined correspondingly to a distance between the scan positions at which said positive and negative peaks occur.

9. A surface defect tester as claimed in claim 8, wherein said scan positions are obtained as two dimensional coordinates, wherein the detection position of said defect is set substantially at a center position between the scan positions at which said positive and negative peaks occur and wherein a continuity of a certain defect to another defect is determined from a distance between said center position and the distance of said scan positions and said certain defect and said another defect are grouped as one defect.

10. A surface defect tester as claimed in claim 8, further comprising a second light receiver composed of m light receiving elements arranged in one direction for generating m light receiving signals, where m is an integer equal to or larger than 2, wherein the major axis of said ellipsoidal image on said first light receiver corresponds to the circumferential direction of said disk and wherein a major axis of said ellipsoidal image of said second light receiver corresponds to a radial direction of said disk.

11. A surface defect tester as claimed in claim 10, wherein said defect detector receives the light receiving signals from said m light receiving elements and detects a defect corresponding to said m light receiving elements on the basis of said light receiving signals.

12. A surface defect tester as claimed in claim 11, further comprising n amplifiers for amplifying said respective n light receiving signals and A/D converter circuits for converting said n light receiving signals amplified by said n respective amplifiers, wherein said defect detector includes a data processor, said data processor being responsive to the n digital data from said A/D converter circuits to calculate said difference between the total value of levels of the light receiving signals from said light receiving elements on said one side and the total value of levels of the light receiving signals from said the other side and detect said positive and negative peaks of said defect detection signal on the basis of said difference.

13. A surface defect tester as claimed in claim 12, wherein said data processor calculates a center position of said scan positions and the distance between said scan positions to determine the continuity of defect and groups defects, which are determined as continuous, and determines the grouped defects as one defect.

14. A surface defect tester as claimed in claim 13, wherein said data processor calculates an area of said grouped defects as said one defect and determine the size of said grouped defects on the basis of the thus calculated area.

15. A surface defect tester as claimed in claim 10, further comprising n+m amplifiers for amplifying said respective n+m light receiving signals and A/D converter circuits for converting said n light receiving signals amplified by said n respective amplifiers and a data processor responsive to the n+m digital data from said A/D converter circuits, wherein said data processor calculates said difference between the total value of levels of the light receiving signals from said light receiving elements on said one side and the total value of levels of the light receiving signals from said the other side and detects said positive and negative peaks of said defect detection signal on the basis of said difference.

* * * * *